United States Patent [19]

Rosenbaum et al.

[11] Patent Number: 4,473,550

[45] Date of Patent: Sep. 25, 1984

[54] BACTERICIDAL COMPOSITIONS AND METHODS

[76] Inventors: Robert S. Rosenbaum, 57 Broadlawn Pr., West Roxbury, Mass.; Jack Kessler, 568 Clarendon St., Syracuse, N.Y.

[21] Appl. No.: 455,420

[22] Filed: Jan. 3, 1983

Related U.S. Application Data

[62] Division of Ser. No. 225,762, Jan. 16, 1981, abandoned.

[51] Int. Cl.³ .................... A61K 37/48; A61K 33/40; A61K 31/075; C12P 19/56
[52] U.S. Cl. ........................................ 424/94; 424/130; 424/230; 424/258; 424/274; 424/317; 424/319; 424/330; 424/338; 435/78; 435/264
[58] Field of Search ................ 424/50, 53, 94, 130, 424/230, 258, 274, 317, 319, 330, 338; 435/78, 264

[56] References Cited

U.S. PATENT DOCUMENTS

| | | | |
|---|---|---|---|
| 959,605 | 5/1910 | Queisser | 424/53 |
| 2,527,686 | 10/1950 | Sandberg | 424/58 |
| 2,554,464 | 5/1951 | Kraus | 424/53 |
| 3,829,329 | 8/1974 | O'Driscoll et al. | 424/130 |
| 4,150,113 | 4/1979 | Hoogendoorn et al. | 424/50 |
| 4,154,815 | 5/1979 | Pader | 424/50 |
| 4,178,362 | 12/1979 | Hoogendoorn et al. | 424/50 |
| 4,269,822 | 5/1981 | Pellio et al. | 424/50 |

OTHER PUBLICATIONS

"Enzymes", Dixon et al., Academic Press Inc., N.Y., 1958, pp. 100–104 & 208.

Elliott, K. A. C., Oxidations Catalysed by Horseradish & Milk Peroxidases, Biochm. J. 26, 1281–1290, (1932).

Sizer, I. W., The Oxidative Inactivation of Poison Ivy Allergens, by Peroxidase, J. Invest. Dermatology, 16, 103–110, (1951).

Wennstrom et al., Effect of Hydrogen Peroxide on Developing Plaque and Gingivitismman; J. Clinical Period, 6, 115–130, (1979).

Primary Examiner—Douglas W. Robinson

[57] ABSTRACT

Bactericidal compositions and methods include the use of a peroxide and a peroxidase in a defined area such as the mouth to rapidly and efficiently kill bacteria. Donor molecules are transformed into bactericidal free radicals which carry out the desired action. The compositions and methods are particularly effective in alleviating gingival disease and periodontal disease.

4 Claims, No Drawings

BACTERICIDAL COMPOSITIONS AND METHODS

This is a division of application Ser. No. 225,762 filed on Jan. 16, 1981 and now abandoned.

BACKGROUND OF THE INVENTION

It has long been known that bacteria play a part in pathogenic dental caries. More recently an abundance of research has implicated bacteria as the causative agents of periodontal disease. Researchers have found a relationship between tooth deposits in periodontal disease. In 1965 a causal relationship was demonstrated between the daily accumulation of dental plaque which causes gingivitis. Others demonstrated in dogs that gingivitis if untreated progresses to periodontitis. Some different organisms are involved in gingivitis than those involved in periodontal disease. However, the organisms are in both cases various strains and types of bacteria.

To date, the art of treating caries, gingival and periodontal diseases is primarily surgical although some advances have been made in the control of disease by chemical means. Historically, the use of a toothbrush with dental floss has been recognized as a prevention and a treatment of the initial carious and gingival lesions. However, once the lesions progress beyond their initial stages surgical intervention is the treatment of choice. In the treatment of caries the lesion is excised using a rotating carbide steel or diamond burr mounted in a high speed handpiece. The cavity preparation is designed to accommodate a silver amalgam, gold or composite type of filling material which simulates the physiologic architecture of the tooth. In the treatment of periodontal diseases the goal of treatment is to remove tooth deposits with hand scalers and currettes and to surgically excise the periodontal pocket so the pocket is unavailable to foster growth of microorganisms.

Significant advances have been made in the field of preventative cariology through the employment of fluoride containing dentifrices and through the use of viscous polymers which are painted into the pits and fissures of the crown to obliterate these niches where routine oral hygiene practices are ineffective. The purpose of using fluoride as a nutritional supplement or as a topical agent is to incorporate fluoride into the hydroxyappetite crystalline structure of the enamel. This makes for a more symmetrical and perfect crystal structure which is more resistant to acid demineralization.

Plastic polymeric materials have been shown to be effective in preventing caries by painting them into pits and fissures soon after the eruption of each tooth into the oral cavity. This system works by etching the enamel surface with an acid to leach out surface enamel crystals and make a porous enamel surface. The viscous polymeric materials are painted onto the porous enamel surface and form an intimate mechanical bond with the enamel. Disadvantages of the polymer system include the necessary application of the material immediately after the eruption of the tooth, their propensity to dissolve and abraid and the cost of application.

The control of gingival and periodontal diseases via chemical means has had less success; although, many compounds both in literature and the patent have been proposed for inclusion in dentrifices or mouthwashes. At the present time several chemicals are being considered for their efficacy in preventing or treating periodontal diseases, but there is no accepted therapeutic which is universally recommended by the dental profession. Among such compound considered for use are quatenary ammonium salts, ceramide peroxide, chlorhexidine, systemic and topical antibiotics, alexidine and other compounds having bactericidal efficacy. This approach recognizes that killing plaque bacteria controls caries, gingival and periodontal diseases.

The bactericidal properties of hydrogen peroxide are due to its dissociation into hydroxyl radicals which are toxic to bacteria. This property led long ago to consideration for its use in an oral dentifrice (U.S. Pat. No. 959,605, U.S. Pat. No. 975,814). However, The peroxide containing dentifrices of the prior art were not universally believed effective bactericides. Recent research had led to the proposal that the reason for their ineffectiveness was the slow dissociation of hydrogen peroxide into free radicals when contained in a typical composition. This dissociation is not rapid enough for a sufficient quantity of bactericidal free radicals to be generated during the application of the composition. An enzymatic method of generating hydrogen peroxide in situ (U.S. Pat. Nos. 4,150,113 and 4,178,362) attempted to overcome this problem by directing the formation of hydrogen peroxide to specific areas. However, this system does not appear to have gained widespread acceptance.

An alternate approach to the problem is to disrupt and eliminate the plaque matrix with compounds or enzymes which can affect this result. To this end, a variety of lipases, hydrolases, invertases and proteases, alone and in combination with each other as well as other compounds have been used (U.S. Pat. No. 3,235,460, U.S. Pat. No. 3,194,738, U.S. Pat. No. 4,154,815, U.S. Pat. No. 2,527,686, U.S. Pat. No. 4,155,868). The main drawback to all of these admixtures is the long period of time that they need to be in contact with the tooth surface.

SUMMARY OF THE INVENTION

It is and object of this invention to provide a method of producing bactericidal, free radicals in defined areas in short time periods at effective concentrations by applying a combination of a peroxidase and a peroxide for mixture with donor molecules to obtain the desired free radicals.

Still another object of this invention is to provide a method in accordance with the preceding object which is carried out by the use of a mixture of a peroxidase, a peroxide and a donor molecule.

Still another object of this invention is to provide a composition comprising a mixture of a peroxidase, a peroxide and donor molecules for use in treating diseases of the mouth of mammals to alleviate problems of formation of dental caries, gingivitis and periodontal disease.

Still another object of this invention is to provide the compositions of this invention for mixture with conventional mouth treating materials for use in a preventive maintenance program against oral cavity bacterial disease.

Still another object of this invention is to provide a means and method of killing bacteria and aiding in sterilizing contact lenses by the use of a unique contact lens soaking solution.

According to the invention bactericidal free radicals are produced in a defined area in a short time period at an effective concentration by applying a combination of a peroxidase and a peroxide in the defined area to rapidly and efficiently form bactericidal free radicals. Preferably donor molecules are admixed with the admixed peroxidase and peroxide to give the bactericidal action although in some case, the bacterial metabolites present can act as the donor molecules. Preferably a carrier such as water is used although the admixture can be in various forms including paste, gels, powders and the like.

The method is preferably carried out to alleviate and treat bacterial diseases in the oral cavity as for example to aid in the prevention of dental caries, periodontal disease and gingivitis as well as the alleviation of periodontal disease and gingivitis sometimes when coupled with other standard treating procedures in mammals and man. The method can also be carried out in the defined area of a contact lens to have a bactericidal action and aid in sterilizing contact lenses.

A novel combination of this invention includes an admixture of a peroxidase and a peroxide along with a donor molecule in an amount effective to provide bactericidal free radicals at effective concentrations in the oral cavity without adversely affecting the oral cavity or causing harm thereto.

It is a feature of this invention that the compositions can be provided in standard materials used by humans in the oral cavity. For example, toothpastes, mouthwash materials, tooth powder, chewing gum, prophylaxis paste, denture cleaner and the like can have the materials of this invention incorporated therein. Because of the good bactericidal action of the compositions of this invention and the rapid time period for production of these bactericidal free radicals, the invention is particularly effective to kill bacteria in the mouth and in certain other uses. For example, the compositions and method of this invention can be used in connection with the rapid and efficient cleaning of contact lenses and can act as a sterilizing solution for contact lenses worn in the eye. It is a feature of this invention that a dental substance is provided which has the capacity to kill oral microorganisms including those within plaque which are responsible for dental caries, gingival diseases and periodontal diseases. The invention differs from the prior art application of hydrogen peroxide to the mouth in that the peroxidase used unlike the prior art provides rapid and efficient production of bactericidal action in concentrations high enough to give advantageous results in the mouth of the user without the necessity to use conditions or concentrations of peroxide which would be injurious to health.

DESCRIPTION OF THE PREFERRED EMBODIMENTS

The material used as a bactericidal material in accordance with this invention is preferably a combination of at least a peroxide and a peroxidase but preferably peroxide, peroxidase and donor molecules which are capable of being transformed into bactericidal free radicals.

The admixture is preferably used in a carrier liquid or paste. Standard carriers can be used. In liquid form, water is the preferred carrier but any fluid non-reactive with the components of the admixture and compatible with the physiology of the mouth or other defined area in which the material is to be used, can be employed. For example, the carrier can be water, toothpaste of standard formulation, mouthwash of standard formulation, chewing gum, prophylaxis paste, denture cleaner, oral cleansing gels and the like.

The admixture can be used in a dry form after first lyophilizing the material. When this is done, all components can be mixed together and activated by introduction into the mouth or other defined area or first dissolving the material in a carrier such as water. When other than dry form materials are used and even in that case, it is preferred to use two part formulations. Standard containers such as toothpaste tubes having two compartments can be used. It is best to separate the peroxidase and the peroxide prior to introduction into the defined area to be treated since these materials will react with each other particularly when in dispersed form in a carrier such as water.

The system of this invention incorporates the peroxide and an acceptor molecule. The enzyme peroxidase catalyzes transfer of electrons from donor molecules to acceptor molecules. When an electron is removed from the donor molecule, this molecule is transformed into a bactericidal free radical. A cycle of the enzyme mechanism is illustrated below:

| Step 1 | Enzyme | + | ROOH | OR Enzyme$_1$ | + | H$_2$O |
|---|---|---|---|---|---|---|
| Step 2 | OR Enzyme$_1$ | + | AH$_1$ | OR Enzyme$_2$ | + | A· |
| Step 3 | OR Enzyme$_2$ | + | AH$_2$ | Enzyme | + | A· + ROH |

Where R = CH$_3$, CH$_3$CH$_2$, H
AH = donor molecule
A· = free radical of donor molecular The increased rate of formation of radicals produced by this chemical system allows for rapid generation of high concentrations of bactericidal free radicals in defined areas of an oral cavity or other locations. For example, when a solution is used, the system can be particularly effective in the cleaning and sterilizing of contact lenses after removal from the eye, as for example, after daily use.

The peroxide in this invention is preferably hydrogen peroxide since it reacts rapidly and is relatively inexpensive. However, other peroxides can be used as for example methyl peroxide and ethyl peroxide. Other peroxides can be used although often the cost is increased and no added advantage is obtained.

The peroxidase used can be obtained from a wide variety of sources and is identified by the IUB and IUPAC, Enzyme Commission identification No. E.C. 1.11.1.7. Peroxidase, which uses a peroxide as an acceptor molecule, imparts to the bactericidal composition of this invention an enormous catalytic advantage in generating active constituents capable of killing selected bacteria in defined areas. A high concentration of free radicals are produced in short time periods for example, the reaction rate to form free radicals occurs essentially instantaneously and proceeds at a rapid rate slowing down at least 50% within a 10 minute time period for a typical formulation. The peroxidase can come from a wide variety of sources and can be isolated by any of the well-known prior art procedures as used by several companies which offer a peroxidase for sale. The use of horseradish peroxidase is preferred since it is easily isolated, has low cost, and has very high stability giving it a long lifetime. Peroxidases have variable substrate specificities depending upon their source of isolation. Hydrogen peroxide is often the most effective substrate. However, methyl and ethyl peroxide are often acceptable and in some cases other peroxides can be used.

The donor molecules are organic molecules which can be acted upon to aid in formation of bactericidal free radicals. Many donor molecules can be used as will be recognized by those skilled in the art. In some cases the bacterial metabolites to be acted on as in the mouth can themselves form the donor molecules for the invention when admixed with the system of this invention. However, in the preferred embodiments, it is preferred to add donor molecules which have good stability with high reactivity. The following materials are particularly suitable: phenylethylamine, tyrosine, tryptophan, benzoic acid, salicyclic acid, hydroquinone, dehydrophenylalanine, vanillan and para-aminobenzoic acid.

Different donor molecules have different abilities and reactivities and can be selected to focus bactericidal selectivity on any given preparation by careful selection of donor molecules or by designing specific donor molecules with high selectivity for specific bacteria.

A prerequisite for the storage of any preparation is not allowing all three components (donor molecules, acceptor molecules and peroxidase) of the system to combine under conditions where the catalytic process can occur. The combination of these components under such conditions will precipitate the depletion of the enzyme's substrate molecules and thereby attenuate the effectiveness of the preparation. In any event the activity of the peroxidase will usually be between 0.050 and 50 units per cubic centimeter of the composition. By one unit of enzyme activity is meant that quantity of enzyme which will convert the conversion of 1 micromole of substrate (i.e. peroxide) per minute at 37 degrees C, pH 6.0 in 10 mM sodium phosphate.

The quantity of enzyme used can vary depending upon the specific formulation and its use but is preferably between $1 \times 10^{-3}$ and $1 \times 10^{-1}$ mg. of protein per cubic centimeter of the composition in which it was used.

EXAMPLE I

A mouthwash was formed by admixture of the following:

Methyl Cellulose: 1.0% by weight of composition
Aromatic Flavoring: 1.0% by weight of composition
Tyrosine: 0.50% by weight of composition
Sodium Dodecyl Sulfate: 1.25% by weight of composition
Sodium peroxide: 1.0% by weight of composition
Sodium benzoate: 0.5% by weight of composition
Para-aminobenzoic acid: 0.40% by weight of composition
Distilled water: up to 100% by weight of composition To evaluate the effect this preparation has on a mixed population of human plaque bacteria, samples were collected from a patient's untreated periodontal pocket for subsequent studies. The sodium peroxide breaks down to form hydrogen peroxide in water. The plaque samples were diluted in prereduced anerobic solution, sonicated and plated on BMB media (Scott) which is a strict anerobic medium and incubated in a conventional anerobic jar. Plate 1 was streaked with the diluted and sonicated sample. Plate 2 contained the ingredients of the mouthwash except for peroxidase as well as streaked sample. Plate 3 contained all of the ingredients listed above including horseradish peroxidase mixed with the mouthwash in an amount of $1 \times 10^{-2}$ mg/ml as well as streaked sample. Plates were grown for five days at 37 degrees C. and the number of colonies on each plate were counted at this time. The number of colonies for each of five trials are indicated below:

| Plate | Trial Number | | | | |
|---|---|---|---|---|---|
| | 1 | 2 | 3 | 4 | 5 |
| 1 | 40 | 48 | 32 | 26 | 55 |
| 2 | 7 | 2 | 8 | 13 | 6 |
| 3 | 0 | 0 | 0 | 0 | 0 |

The results indicate that the complete formulations offer a substantial increase in bactericidal efficiency relative to the use of hydrogen peroxide.

EXAMPLE II

A toothpaste is formed having the following composition by weight of the composition:

| | |
|---|---|
| Silica | 30% |
| Paraffin | 10% |
| Sorbitol (70% in water) | 40% |
| Sodium Dodecyl Sulfate | 2.5% |
| Coloring substances, flavoring substances, sweetener, preservative | 2.4% |
| Sodium fluoride | 0.1% |
| Sodium bicarbonate | 5.0% |
| Hydrogen Peroxide | 10% |

Into a first chamber of toothpaste having the above composition was incorporated peroxidase in an amount of 50 units per cubic centimeter of the paste and into a second chamber containing the base paste was incorporated tyrosine in an amount of 0.20 grams per cubic centimeter of paste. Whe admixed and used as a toothpaste in the mouth, good bactericidal action is obtained.

When the toothpaste is stored at 37 degrees C. for thirty days the enzyme activity declined from the initial level of 50 units per cubic centimeter to 42 units per cubic centimeter, indicating satisfactory stability.

EXAMPLE III

Following is the composition of another toothpaste falling within the invention.

Aluminum Hydroxide: 40% by weight of entire composition
Sorbitol: 30% by weight of entire composition
Sodium Dodecyl Sulfate: 2% by weight of entire composition
Sodium fluoride: 0.1% by weight of entire composition
Hydrogen Peroxide: 3% by weight of entire composition
Coloring substances, flavoring substances, Sweetener, preservative: 2.5% of entire composition
Water: 22.4% by weight of entire composition Into chamber A of a toothpaste having the above composition was incorporated a peroxidase in an amount of 4.5 units per cubic centimeter of the paste and into chamber B was incorporated para-aminobenzoic acid in an amount of 0.25 grams per cubic centimeter of paste. When admixed as by placing equal amounts of chamber A contents and chamber B contents on a toothbrush and brushing, good bactericidal properties are found.

The peroxidase of toothpaste under number III does not lose any measurable activity after a period of 20 days at the storage temperature of 4 degrees C.

EXAMPLE IV

A contact lens soaking solution can be formed by admixing the following, given in % by weight of the total composition:

| | |
|---|---|
| NaCl - Sodium Chloride | 0.90% |
| Para-aminobenzoic acid | 0.40% |
| Sodium Peroxide | 4.5% |
| Peroxidase (horseradish) | 0.001% |

The above materials, all sterile, are stored in a sterile pocket. The pocket is opened and added to a sufficient amount of sterile water (10 ml) to make the above concentrations, that is, 0.09 grams of Nacl, 0.04 grams of PABA, etc. added to 10 ml of sterile water. A plastic contact lens, hard or soft is immersed in this solution for 10 minutes. The contact lens is then rinsed with sterile wetting solution to remove the residual amounts of constituents present, and is then ready for use.

When compositions are formulated as above described, they are of help in reducing unwanted bacteria in the oral cavity and/or on the surfaces of hard and soft contact lenses.

While specific embodiments have been shown and described, many variations are possible. In all cases, where the materials are to be used in the oral cavity, they are compatible with the body and do not cause unwanted destruction to the body. For example the pH is such that it will not change the pH of the mouth out of a range of about from 6.7 to 7.4. The material is non-toxic to man and animals. Standard stabilizers, colorants, carriers and the like can be used.

Common ingredients of toothpaste to which the bactericidal compositions of this inention can be added include bases in amounts of from 10 to 50% by weight, colorants in amounts of from 1 to 2% by weight, fragrances or flavorants in amounts of 1 to 2% by weight and stabilizers in amounts of less than 1% by weight.

Suitable bases include sorbitol, glycerin, cellulose gum and carrageen. Suitable abrasives include silica, alumina, hydroxide, sodium silicate, sodium metaphosphate and magnesium aluminum silicate. Suitable colorants include titanium dioxide, FD and C Blue No. 1, FD and C Yellow No. 10. Suitable fragrances include spearmint, peppermint, lime, mint, sodium saccharin. Stabilizers include sodium benzoate. Many equivalent ingredients can be used.

Preferably mixtures of the present invention are made just prior to addition to the defined area where the bactericidal effect is to take place. Such admixtures preferably have from 0.050 to 50 units per cubic centimeter of a peroxidase, 0.5 to 30% by weight of peroxide and 0.5 to 10% by weight of a donor molecule when used. Hydrogen peroxide is preferably not permitted to be more than a 3% aqueous solution for oral, topical application in order to prevent irritation to the skin. This combination of can be further admixed with other formulas such as toothpaste, tooth powder, gels and the like where the amount of the combination in the overall formulation can vary greatly. Thus the carrier for the formulation can be water or other liquids or pastes.

In order to avoid contact of free radicals to sensitive tissues, such as the cornea of the eye, it is wise to rinse the sterilized contact lenses for five minutes in sterile water. In all cases, the components of the admixture used are such as to enable the bactericidal action to take place in 10 minutes or less at concentrations high enough to be effective without being harmful to the body or to material being treated.

We claim:

1. A method for disinfecting a contact lens comprising forming a bactericide having a limited period of bacteriological activity, said bactericide comprising at least three components including a peroxide generated on dissolution in water slected from the group consisting of hydrogen peroxide, sodium peroxide, methyl peroxide and ethyl peroxide, a peroxidase within the classification E.C. 1.11.1-7 and a source of predetermined donor molecules adopted to act as a substrate for said peroxidase, with each of the three components being in a dry state such that the bactericide is inactive; admixing the three components in a liquid carrier solution to cause a catalyzed reaction by said peroxidase for generating free radicals from said source of donor molecules, immersing the contact lens into said solution substantially simultaneous with the admixture of all three components whereby bacteria present on said contact lens will be killed during said limited period of bacteriological activity.

2. A method as defined in claim 1 wherein said peroxidase is horseradish peroxidase.

3. A method as defined in claim 2 wherein said source of donor molecules is selected from the class consisting of phenylethylamine, tyrosine, tryptophan, benzoic acid, salicyclic acid, hydroquinone, dehydrophenylalanine, vanillin and para-aminobenzoic acid.

4. A method as defined in claim 3 wherein said peroxide is hydrogen peroxide.

* * * * *